(12) United States Patent
Kamal et al.

(10) Patent No.: US 10,947,248 B2
(45) Date of Patent: Mar. 16, 2021

(54) 4β-AMIDOTRIAZOLE LINKED PODOPHYLLOTOXIN DERIVATIVES AS POTENTIAL ANTICANCER AGENTS

(71) Applicant: COUNCIL OF SCIENTIFIC & INDUSTRIAL RESEARCH, New Delhi (IN)

(72) Inventors: Ahmed Kamal, Hyderabad (IN); Velma Ganga Reddy, Hyderabad (IN); Ayinampudi Venkata Subbarao, Hyderabad (IN); Syed Riyaz, Hyderabad (IN); Vadithe Lakshma Nayak, Hyderabad (IN); Shaik Taj, Hyderabad (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 137 days.

(21) Appl. No.: 16/084,162

(22) PCT Filed: Mar. 10, 2017

(86) PCT No.: PCT/IN2017/050088
§ 371 (c)(1),
(2) Date: Sep. 11, 2018

(87) PCT Pub. No.: WO2017/154026
PCT Pub. Date: Sep. 14, 2017

(65) Prior Publication Data
US 2020/0123171 A1 Apr. 23, 2020

(30) Foreign Application Priority Data
Mar. 11, 2016 (IN) .............................. 201611008486

(51) Int. Cl.
*C07D 493/04* (2006.01)
*A61P 35/00* (2006.01)
*A61P 31/12* (2006.01)

(52) U.S. Cl.
CPC .................................. *C07D 493/04* (2013.01)

(58) Field of Classification Search
CPC ......... C07D 493/04; A61P 35/00; A61P 31/12
See application file for complete search history.

(56) References Cited

PUBLICATIONS

Belani et al., "Etoposide: current status and future perspectives in the management of malignant neoplasms." *J. Cancer Chemother. Pharmacol.*, 1994, 34:S118-S126.
Chen et al., "Semi-Synthesis and Biological Evaluation of 1,2,3-Triazole-Based Podophyllotoxin Congeners as Potent Antitumor Agents Inducing Apoptosis in HepG2 Cells," *Arch. Pharm. Chem. Life. Sci*, 2012, 345(12):945-956.

Chen et al., "Synthesis of 4β-triazole-podophyllotoxin derivatives by azide-alkyne cycloaddition and biological evaluation as potential antitumor agents," *European Journal of Medicinal Chemistry*, 2011, 46(9):4709-4714.
Damayanthi et al., "Podophyllotoxins: current status and recent developments" *Curr. Med. Chem.*, 1998, 5:205-252.
Gordaliza et al., "Antitumor properties of podophyllotoxin and related compounds" *A. Curr. Pharm. Des.*, 2000, 6:1811-1839.
Haider et al., "1,2,3-Triazoles: scaffold with medicinal significance" *Inflammation & Cell Signaling*, 2014, 1:e95.
International Search Report and Written Opinion issued in International Patent Application No. PCT/IN2017/050088, dated Jul. 3, 2017.
Kamal et al., "Synthesis and anticancer activity of heteroaromatic linked 4[beta]-amido podophyllotoxins as apoptotic inducing agents," *Bioorganic & Medicinal Chemistry Letters*, 2012, 23(1):273-280.
Kamal et al., "Synthesis of 4β-amido and 4β-sulphonamido analogues of podophyllotoxin as potential antitumor agents," *Bioorg. Med. Chem.*, 2003, 11:5135-5142.
Lee, Kuo-Hsiung, "Current Developments in the Disvoery and Design of new Drug Candidates from Plant Natural Product Leads" *J. Nat Prod.*, 2004, 67:273-283.

(Continued)

*Primary Examiner* — Sun Jae Yoo
(74) *Attorney, Agent, or Firm* — Norton Rose Fulbright US LLP

(57) ABSTRACT

The present invention relates to a compound of general formula (A). The invention provides asynthesis of new 4β-amidotriazole linked podophyllotoxin derivatives of general formulae 8a-z to 9a-z useful as potential anticancer agents against human cancer cell lines and process for the preparation thereof. Wherein n=0, 1 and $R_1$-$R_5$=[H, Cl, F, $CH_3$, $OCH_3$, 3,4(-$OCH_2$O—), $CF_3$, $OCF_3$, m-$OC_6H_5$, OH]

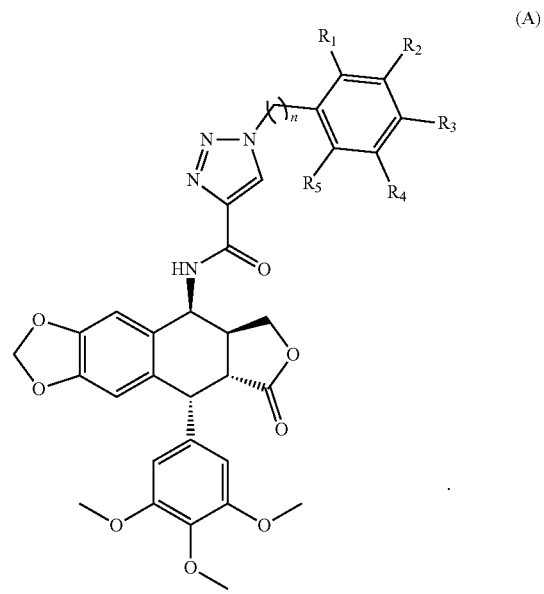

(A)

5 Claims, No Drawings

(56) References Cited

PUBLICATIONS

Macdonald et al., "On the Mechanism of ternaction of DNA topoisomerase II with chemotherapeutic agents" *DNA Topoisomerase in Cancer*. New York: Oxford University Press. 1991:199-214.

Tiew et al., "Inhibition of dengue Virus and West Nile Virus Proteasesby Click Chemsitry-Derived Benz[d]isothiazol-3(2H)-one of Derivatives" *Biorg. Med. Chem.*, 2012, 20:1213-1221.

Zhou et al., "Discovery and biological evaluation of novel 6,7-disubstituted4-(2-fluorophenoxy) quinoline derivatives possessing 1,2,3-triazole-4-carboxamide moiety as c-Met kinase inhibitors," *Bioorg. Med. Chem.*, 2014, 22:6438-6452.

Zilla et al., "A convergent Synthesis of alkyne-azide cycloaddition derivatives of 4-α, β-2-propyne podophyllotoxin depicting potent cytoto" *European Journal of Medicinal Chemistry*, 2014, 77:47-55.

4β-AMIDOTRIAZOLE LINKED PODOPHYLLOTOXIN DERIVATIVES AS POTENTIAL ANTICANCER AGENTS

CROSS-REFERENCE TO RELATED APPLICATIONS

This application is a national phase application under 35 U.S.C. § 371 of International Application No. PCT/IN2017/050088 filed 10 Mar. 2017, which claims priority to Indian Patent Application No. 201611008486 filed 11 Mar. 2016. The entire contents of each of the above-referenced disclosures is specifically incorporated herein by reference without disclaimer.

FIELD OF THE INVENTION

The present invention relates to the synthesis and biological evaluation of 4β-amidotriazole linked podophyllotoxins of general formula A as potential anticancer agents and a process for the preparation thereof

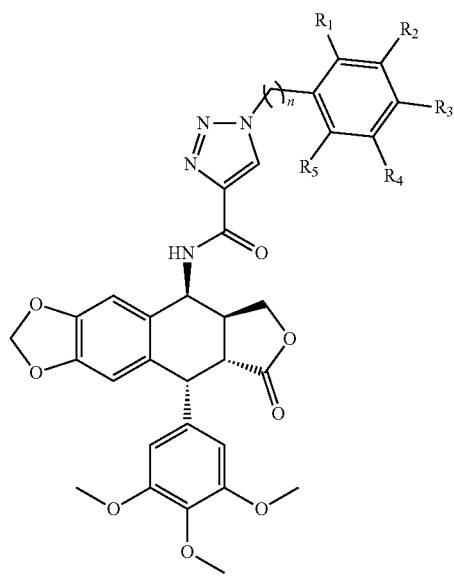

wherein
$R_1$-$R_5$=[H, Cl, F, $CH_3$, $OCH_3$, 3,4(-$OCH_2O$—), $CF_3$, $OCF_3$, m-$OC_6H_5$, OH]; n=0, 1

BACKGROUND OF THE INVENTION

Natural product is the key source of drug discovery and design, almost about 25 percent of prescribed medicines originate from plant sources. Several important anticancer natural products such as vinblastine, vincristine, paclitaxel and the semi-synthetic drugs like etoposide, etopophos and teniposide [K. H. Lee, *J. Nat. Prod.*, 2004, 67, 273-283] are the derivatives of podophyllotoxin, that are isolated mainly from the roots of *podophyllum* species. Surprisingly, these semisynthetic derivatives and the parent compound (podophyllotoxin), show different mechanisms of action. Podophyllotoxin inhibits the assembly of tubulin into microtubules through interaction with the protein at the colchicine binding site, preventing the formation of the spindle. Whereas the semisynthetic derivatives inhibit DNA topoisomerase-II (topo-II) by stabilizing the covalent topoisomerase-II DNA cleavable complex [Macdonald, L. T.; Lehnert, K. E.; Loper, T. J.; Chow, C. K.; Ross, E. W. In DNA Topoisomerases in *Cancer*; Potmesil, M., Kohn, W. K., Eds.; Oxford University: New York, 1991; p 199] and are used against a variety of cancers, including germ-cell malignancies, small-cell lung cancer, non-Hodgkin's lymphoma, leukemia, Kaposi's sarcoma, neuroblastoma and soft tissue sarcoma [Belani, P. C.; Doyle, A. L.; Aisner, *J. Cancer Chemother. Pharmacol.*, 1994, 34, S 118].

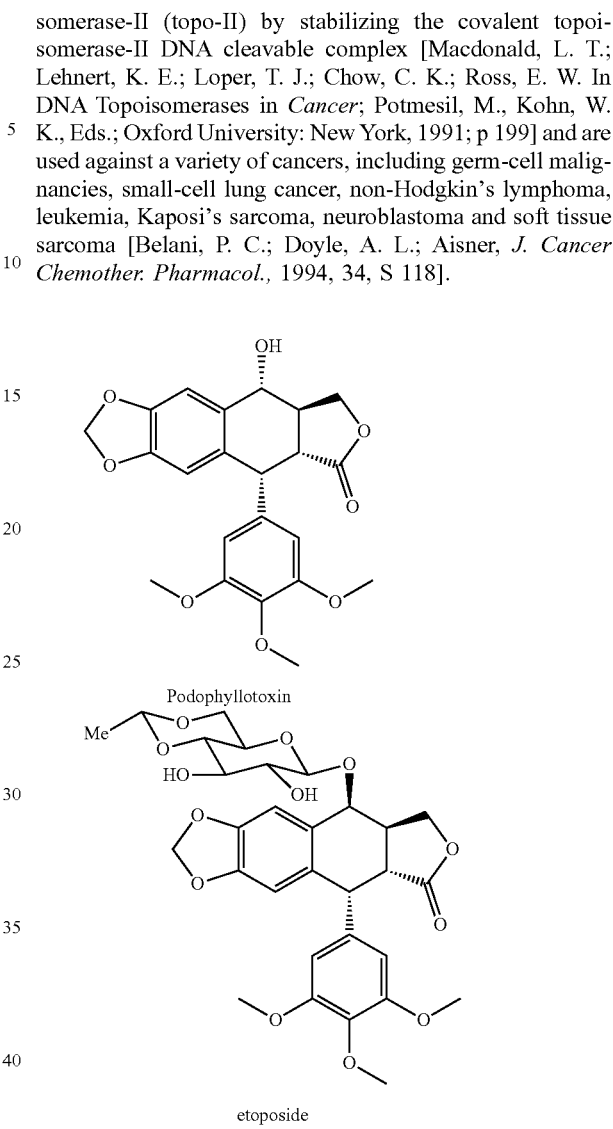

However, their therapeutic use has encountered certain limitations such as acquired drug resistance and lower bioavailability. To overcome such problems, extensive synthetic efforts have been carried out by a number of researchers to improve cytotoxicity as well as DNA topoisomerase-II inhibition. The core structural features like transfused γ-lactone, fused dioxole ring, and the almost orthogonal free-rotating 3,4,5-trimethoxyphenyl fragment are considered essential for cytotoxic activity of podophyllotoxin derivatives. It has also been indicated in the literature that bulky substitution at the C-4 position of the podophyllotoxin usually enhances the cytotoxicity and DNA topoisomerase-II inhibition activity [(a) Damayanthi, Y.; Lown, J. W. Curr. Med. Chem. 1998, 5, 205; (b) Gordaliza, M.; Castro, M. A.; Miguel del Corral, J. M.; San Feliciano, A. *Curr. Pharm. Des.*, 2000, 6, 1811].

On the other hand, 1,2,3-triazoles have a high dipole moment (about 5 D) and are able to participate actively in hydrogen bond formation as well as in dipole-dipole and π stacking interactions which helps them in binding easily with the biological targets and improves their solubility [Saqlain Haider, Mohammad Sarwar Alam, Hinna Hamid. *Inflammation & Cell Signaling.*, 2014; 1: e95].

Based on the these observation we designed and synthesized a series of 4β-amidotriazole linked podophyllotoxin derivatives to improve the solubility as well as cytotoxicity. The present studies show the importance of triazole and amide linkage to the podophyllotoxin scaffold in discovery and development of newer cytotoxic agents. The purpose of the present work involves the synthesis of new molecules based on podophyllotoxin ring system with a view to overcome the limitations of etoposide. One of the major issues of selectivity in the development of anticancer agents can has been addressed by these molecules as they are highly selective towards some specific cancer cell lines.

OBJECTIVES OF THE INVENTION

The main objective of the present invention is to provide 4β-amido substituted triazole linked phodophyllotoxin derivatives 8a-z to 9a-z as potential antitumor agents. Yet another object of this invention is to provide a process for the preparation of new 4β-amidotriazole linked phodophyllotoxin derivatives.

SUMMARY OF THE INVENTION

Accordingly, present invention provides to 4β-amidotriazolelinked phodophyllotoxins of general formulae A

A wherein
$R_1$-$R_5$=[H, Cl, F, $CH_3$, $OCH_3$, 3,4(-$OCH_2O$—), $CF_3$, $OCF_3$, m-$OC_6H_5$, OH]; n=0, 1
n=0, it represents general formulae of A1; and n=1, it represents general formulae of A2.

In an embodiment of the present invention 4β-amido substituted triazole linked podophyllotoxins of general formulae A1 represented by the compounds of general formulae 8a-8z, A2 represented by the compounds of general formulae 9a-9z.
N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1-phenyl-1H-1,2,3-triazole-4-carboxamide (8a)
1-(3-methoxyphenyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (8b)
1-(4-methoxyphenyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (8c)
1-(3,4-dimethoxyphenyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (8d)
1-(3,5-dimethoxyphenyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (8e)
1-(2,4-dimethoxyphenyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (8f)
N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1-(3,4,5-trimethoxyphenyl)-1H-1,2,3-triazole-4-carboxamide (8g)
1-(benzo[d][1,3]dioxol-5-yl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (8h)
1-(4-methoxy-3-methylphenyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (8i)
1-(3-fluoro-4-methoxyphenyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (8j)
1-(3-chloro-4-methoxyphenyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (8k)
N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1-(3-phenoxyphenyl)-1H-1,2,3-triazole-4-carboxamide (8l)
N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1-(3-(trifluoromethyl)phenyl)-1H-1,2,3-triazole-4-carboxamide (8m)
N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1-(4-(trifluoromethyl)phenyl)-1H-1,2,3-triazole-4-carboxamide (8n)
1-(3-chlorophenyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (8o)
1-(4-chlorophenyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (8p)
1-(3-fluorophenyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (8q)

1-(4-fluorophenyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (8r)

N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1-(3-(trifluoromethoxy)phenyl)-1H-1,2,3-triazole-4-carboxamide (8s)

N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1-(4-(trifluoromethoxy)phenyl)-1H-1,2,3-triazole-4-carboxamide (8t)

1-(3,4-difluorophenyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (8u)

1-(3,4-dichlorophenyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (8v)

1-(4-hydroxyphenyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (8w)

N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1-(p-tolyl)-1H-1,2,3-triazole-4-carboxamide (8x)

1-(3-hydroxy-4-methoxyphenyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (8y)

1-(4-chloro-3-fluorophenyl)-N-((5S,5aS,8 aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (8z)

1-benzyl-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (9a)

1-(3-methoxybenzyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (9b)

1-(4-methoxybenzyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (9c)

1-(3,4-dimethoxybenzyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (9d)

1-(3,5-dimethoxybenzyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (9e)

1-(2,4-dimethoxybenzyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (9f)

N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1-(3,4,5-trimethoxybenzyl)-1H-1,2,3-triazole-4-carboxamide (9g)

1-(benzo[d][1,3]dioxol-5-ylmethyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (9h)

1-(3-methoxy-4-methylbenzyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (9i)

1-(3-fluoro-4-methoxybenzyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (9j)

1-(3-chloro-4-methoxybenzyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (9k)

N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1-(3-phenoxybenzyl)-1H-1,2,3-triazole-4-carboxamide (9l)

N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1-(3-(trifluoromethyl)benzyl)-1H-1,2,3-triazole-4-carboxamide (9m)

N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1-(4-(trifluoromethyl)benzyl)-1H-1,2,3-triazole-4-carboxamide (9n)

1-(3-chlorobenzyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (o)

1-(4-chlorobenzyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (9p)

1-(3-fluorobenzyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (9q)

1-(4-fluorobenzyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (9r)

N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1-(3-(trifluoromethoxy)benzyl)-1H-1,2,3-triazole-4-carboxamide (9s)

N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1-(4-(trifluoromethoxy)benzyl)-1H-1,2,3-triazole-4-carboxamide (9t)

1-(3,4-difluorobenzyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (9u)

1-(3,4-dichlorobenzyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (9v)

1-(4-hydroxybenzyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (9w)

1-(4-methylbenzyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (9x)

1-(3-hydroxy-4-methoxybenzyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (9y)

1-(4-chloro-3-fluorobenzyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (9z)

DETAILED DESCRIPTION OF THE INVENTION

The precursors 4β-amino podophyllotoxin formula 7 were prepared using literature method [A. Kamal et al./ *Bioorg. Med. Chem.*, 2003, 11, 5135-5142]. Similarly azidobenzene and (azidomethyl)benzene formula 1a-z and 2a-z were also prepared using literature method [S. Zhou et al. *Bioorg. Med. Chem.*, 2014, 22, 6438-6452; K.-C. Tiew et al./*Bioorg. Med. Chem.*, 2012, 20, 1213-1221]. 4β-amido-triazole linked podophyllotoxin derivatives of formula 8a-z and 9a-z were synthesized as illustrated in the Scheme 1.

i. To a stirred solution of compound ethyl propiolate (1 mmol) with different substituted aliphatic and aromatic azides 1a-z and 2a-z (1.2 mmol) in t-BuOH:H$_2$O (1:1) (20 mL), CuSO$_4$·5H$_2$O catalyst (1 mol %) (3 mmol) and sodium ascorbate (5 mol %) were added and this mixture was stirred for 12 h at room temperature. After completion of the reaction, t-butanol was removed under reduced pressure. Ethyl acetate and water were added to the above residue and stirred for another 30 min, extracted with ethylacetate and the organic layer was separated, dried and evaporated under reduced pressure to afford the crude products. These were further purified by column chromatography using ethyl acetate-hexane (30%) to provide the pure compounds 3a-3z and 4a-4z.
  ii. LiOH·H$_2$O (6.7 mmol) was added in one portion to a solution of ester (4.5 mmol) in THF/water (1:1, 20 mL). The reaction mixture was stirred until the solid had dissolved and was then left overnight at room temperature. The solvents were removed in vacuo, and the residue was dissolved in water (15 mL). The resulting solution was washed with diethyl ether (7 mL). The aqueous layer was concentrated to half of its volume and then acidified with 30% hydrochloric acid (15 mL). The resulting precipitate was filtered and dried to give compounds 5a-5z and 6a-6z (85-90%) as a white powder.
  iii. To a solution of substituted 1-phenyl-1H-1,2,3-triazole-4-carboxylic acids or 1-benzyl-1H-1,2,3-triazole-4-carboxylic acids (5a-5z and 6a-6z, 0.5 mmol) in dry dimethylformamide, EDCI (0.6 mmol) and HOBT (0.6 mmol) were added at 0° C. and the reaction mixture was stirred for 20 min. To the reaction mixture 4β-amino phodophyllotoxin (7, 0.5 mmol) was added and stirred at room temperature for 12 h. The contents of the reaction mixture were poured into ice-cold water (25 mL), extracted with ethyl acetate (3×15.0) and the combined organic phase was washed with brine, dried over anhydrous sodium sulfate, filtered and concentrated in vacuo. The obtained residue was purified by column chromatography using ethyl acetate-hexane (50%) as eluent to furnish pure 4β-amidotriazole linked podophyllotoxin derivatives 8a-8z and 9a-9z in good yields (75-80%).

The synthesis of new congeners as illustrated in scheme 1 which comprise: The acide-amine coupling reaction between 4β-amino podophyllotoxin formula 7 with 1-phenyl-1H-1,2,3-triazole-4-carboxylic acids compounds of formulae 5a-z and 1-benzyl-1H-1,2,3-triazole-4-carboxylic acids compounds of formulae 6a-z for the compounds (8a-8z to 9a-9z), respectively. These newer triazolo linked podophyllotoxins showed promising cytotoxic activity in various cancer cell lines.

1. Stirring the acids at 0° C. and add amine slowly to the reaction mixture, maintain for 12 h at 0° C.-rt to obtain the compounds (8a-z and 9a-z) respectively.
  2. Synthesis of aryl and benzyle triazolic acids 5a-z and 6a-z.
  3. Purified by the column chromatography using different solvents like ethyl acetate and hexane.

Scheme 1

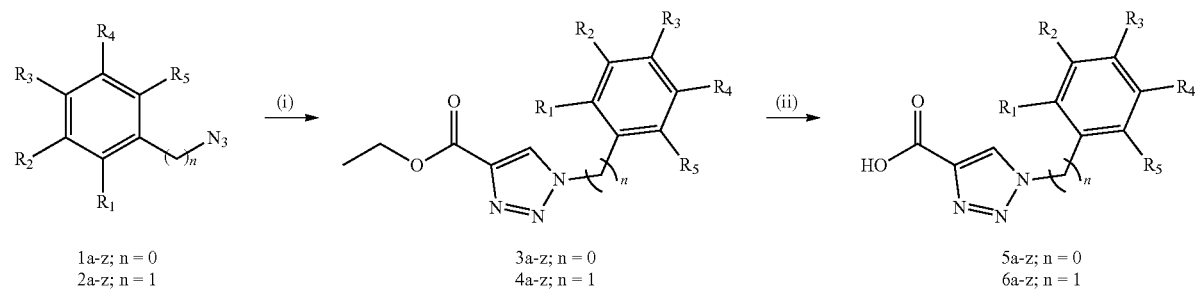

1a-z; n = 0
2a-z; n = 1

3a-z; n = 0
4a-z; n = 1

5a-z; n = 0
6a-z; n = 1

-continued

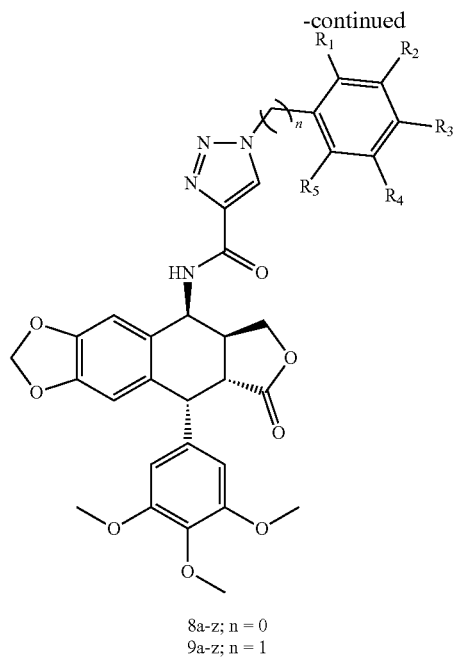

8a-z; n = 0
9a-z; n = 1

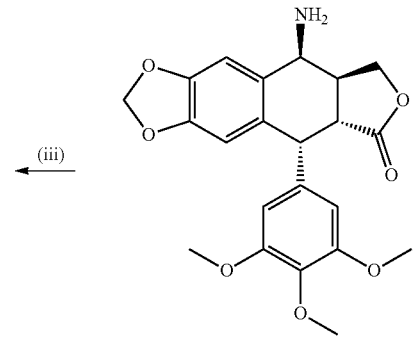

7 wherein
$R_1$-$R_5$=[H, Cl, F, $CH_3$, $OCH_3$, 3,4(-$OCH_2O$—), $CF_3$, $OCF_3$, m-$OC_6H_5$, OH]

Reagents and conditions: (i) Ethyl propiolate, different substituted aliphatic/aromatic azides, $CuSO_4 \cdot 5H_2O$, sodium ascorbate, t-BuOH/$H_2O$ (1:1), rt, 12 h; (ii) LiOH, THF:$H_2O$ (1:1), rt, overnight; (iii) DMF, EDC, HOBt, 4β-amino podophyllotoxin, 0° C.-rt, 12 h.

EXAMPLES

The following examples are given by way of illustration of the working of the invention in actual practice and therefore should not be construed to limit the scope of present invention.

Example 1

N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1-phenyl-1H-1,2,3-triazole-4-carboxamide (8a)

To a solution of 1-phenyl-1H-1,2,3-triazole-4-carboxylic acid (94.5 mg, 0.5 mmol) in dry dimethylformamide, EDCI (115 mg, 0.6 mmol) and HOBT (81 mg, 0.6 mmol) were added at 0° C. and the reaction mixture was stirred for 20 min. To the reaction mixture 4β-amino phodophyllotoxin (206.5 mg, 0.5 mmol) was added and stirred at room temperature for 12 h. The contents of the reaction mixture were poured into ice-cold water (25 mL), extracted with ethyl acetate (3×15.0) and the combined organic phase was washed with brine, dried over anhydrous sodium sulfate, filtered and concentrated in vacuo. The obtained residue was purified by column chromatography using ethyl acetate-hexane (0-50%) as eluent to give 215 mg (75%) of analytically pure compound (8a). mp: 170-172° C.; $[a]^{25}_D$: −86.0 (c: 3.6, $CHCl_3$); $^1$H NMR ($CDCl_3$): δ 8.54 (s, 1H), 7.76 (d, J=7.55, 2H), 7.64-7.50 (m, 5H), 6.84 (s, 1H), 6.49 (s, 1H), 5.99 (d, J=3.5 Hz, 2H), 5.45 (dd, J=3.39, 7.16 Hz, 1H), 4.58 (d, J=3.21 Hz, 1H), 4.49 (t, J=6.79 Hz, 1H), 3.98 (d, J=8.87 Hz, 1H), 3.81 (s, 3H), 3.75 (s, 6H), 3.10 (d, J=3.02 Hz, 2H); MS (ESI): m/z 585 [M+H]$^+$.

Example 2

1-(4-methoxyphenyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (8c)

To a solution of 1-(4-methoxyphenyl)-1H-1,2,3-triazole-4-carboxylic acid (109.5 mg, 0.5 mmol) in dry dimethylformamide, EDCI (115 mg, 0.6 mmol) and HOBT (81 mg, 0.6 mmol) were added at 0° C. and the reaction mixture was stirred for 20 min. To the reaction mixture 4β-amino phodophyllotoxin (206.5 mg, 0.5 mmol) was added and stirred at room temperature for 12 h. The contents of the reaction mixture were poured into ice-cold water (25 mL), extracted with ethyl acetate (3×15.0) and the combined organic phase was washed with brine, dried over anhydrous sodium sulfate, filtered and concentrated in vacuo. The obtained residue was purified by column chromatography using ethyl acetate-hexane (0-50%) as eluent to give 238 mg (76%) of analytically pure compound (8c). mp: 195-197° C.; $[a]^{25}_D$: −77.6 (c: 3.2, $CHCl_3$); $^1$H NMR ($CDCl_3$): δ 8.43 (s, 1H), 7.65 (d, J=9.0 Hz, 2H), 7.58 (d, J=7.47 Hz, 1H), 7.08 (d, J=9.0 Hz, 2H), 6.83 (s, 1H), 6.47 (s, 1H), 6.30 (s, 2H), 6.00 (d, J=6.56 Hz, 1H), 5.45 (dd, J=4.12, 7.47 Hz, 1H), 4.57 (d, J=4.57 Hz, 1H), 4.49 (dd, J=7.17, 9.30 Hz, 1H), 3.95 (t, J=10.07 Hz, 1H), 3.89 (s, 3H), 3.81 (s, 3H), 3.75 (s, 6H), 3.11-3.03 (m, 2H); MS (ESI): m/z 615 [M+H]$^+$.

Example 3

1-(3,5-dimethoxyphenyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (8e)

To a solution of 1-(3,4-dimethoxyphenyl)-1H-1,2,3-triazole-4-carboxylic acid (124.5 mg, 0.5 mmol) in dry dimethylformamide, EDCI (115 mg, 0.6 mmol) and HOBT (81 mg, 0.6 mmol) were added at 0° C. and the reaction mixture was stirred for 20 min. To the reaction mixture 4β-amino phodophyllotoxin (206.5 mg, 0.5 mmol) was added and stirred at room temperature for 12 h. The contents of the reaction mixture were poured into ice-cold water (25 mL), extracted with ethyl acetate (3×15.0) and the combined organic phase was washed with brine, dried over anhydrous sodium sulfate, filtered and concentrated in vacuo. The obtained residue was purified by column chromatography using ethyl acetate-hexane (0-50%) as eluent to give 249 mg (77%) of analytically pure compound (8e). mp: 145-148° C.; $[\alpha]^{25}_D$: −78.7 (c:3.8, CHCl3); $^1$H NMR (CDCl3): δ 8.51 (s, 1H), 7.71 (d, J=7.47 Hz, 1H), 6.92 (d, J=2.13 Hz, 2H), 6.84 (s, 1H), 6.58 (t, J=2.13 Hz, 1H), 6.42 (s, 1H), 6.28 (s, 2H), 6.00 (d, J=2.44 Hz, 2H), 5.45 (dd, J=4.42, 7.47 Hz, 1H), 4.54 (d, J=4.88 Hz, 1H), 4.49 (q, J=7.47, 9.00 Hz, 1H), 3.94 (t, J=9.46 Hz, 1H), 3.89 (s, 6H), 3.81 (s, 3H), 3.75 (s, 6H), 3.16 (dd, J=5.18, 14.34 Hz, 1H), 3.10-3.02 (m, 1H); MS (ESI): m/z 645 [M+H]$^+$.

Example 4

N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1-(3,4,5-trimethoxyphenyl)-1H-1,2,3-triazole-4-carboxamide (8g)

To a solution of 1-(3,4,5-trimethoxyphenyl)-1H-1,2,3-triazole-4-carboxylic acid (139.5 mg, 0.5 mmol) in dry dimethylformamide, EDCI (115 mg, 0.6 mmol) and HOBT (81 mg, 0.6 mmol) were added at 0° C. and the reaction mixture was stirred for 20 min. To the reaction mixture 4β-amino phodophyllotoxin (206.5 mg, 0.5 mmol) was added and stirred at room temperature for 12 h. The contents of the reaction mixture were poured into ice-cold water (25 mL), extracted with ethyl acetate (3×15.0) and the combined organic phase was washed with brine, dried over anhydrous sodium sulfate, filtered and concentrated in vacuo. The obtained residue was purified by column chromatography using ethyl acetate-hexane (0-50%) as eluent to give 264 mg (78%) of analytically pure compound (8g). mp: 181-183° C.; $[\alpha]^{25}_D$: −83.1 (c:5.9, CHCl3); $^1$H NMR (CDCl3): δ 8.49 (s, 1H), 7.69 (d, J=7.47 Hz, 1H), 6.97 (s, 2H), 6.85 (s, 1H), 6.43 (s, 1H), 6.28 (s, 2H), 6.01 (dd, J=1.37, 2.13 Hz, 2H), 5.45 (dd, J=4.42, 7.47 Hz, 1H), 4.54 (d, J=4.88 Hz, 1H), 4.49 (q, J=7.47, 9.15 Hz, 1H), 3.97 (s, 6H), 3.94 (d, J=1.37 Hz, 1H), 3.91 (s, 3H), 3.81 (s, 3H), 3.75 (s, 6H), 3.15 (dd, J=4.88, 14.34 Hz, 1H), 3.11-3.03 (m, 1H); MS (ESI): m/z 675 [M+H]$^+$.

Example 5

1-(benzo[d][1,3]dioxol-5-yl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (8h)

To a solution of 1-(benzo[d][1,3]dioxol-5-yl)-1H-1,2,3-triazole-4-carboxylic acid (116.5 mg, 0.5 mmol) in dry dimethylformamide, EDCI (115 mg, 0.6 mmol) and HOBT (81 mg, 0.6 mmol) were added at 0° C. and the reaction mixture was stirred for 20 min. To the reaction mixture 4β-amino phodophyllotoxin (206.5 mg, 0.5 mmol) was added and stirred at room temperature for 12 h. The contents of the reaction mixture were poured into ice-cold water (25 mL), extracted with ethyl acetate (3×15.0) and the combined organic phase was washed with brine, dried over anhydrous sodium sulfate, filtered and concentrated in vacuo. The obtained residue was purified by column chromatography using ethyl acetate-hexane (0-50%) as eluent to give 242 mg (77%) of analytically pure compound (8h). mp: 188-191° C.; $[\alpha]^{25}_D$: −54.6 (c:4.6, CHCl3); $^1$H NMR (CDCl3): δ 8.42 (s, 1H), 7.46 (d, J=7.45 Hz, 1H), 7.23 (d, J=2.07 Hz, 1H), 7.16 (dd, J=2.07, 8.31 Hz, 1H), 6.95 (d, J=8.31 Hz, 1H), 6.82 (s, 1H), 6.54 (s, 1H), 6.32 (s, 2H), 6.11 (s, 2H), 5.99 (d, J=7.21 Hz, 2H), 5.45 (dd, J=2.81, 6.96 Hz, 1H), 4.64 (d, J=2.07 Hz, 1H), 4.52-4.46 (m, 1H), 3.97-3.91 (m, 1H), 3.82 (s, 3H), 3.76 (s, 6H), 3.09-3.05 (m, 2H); MS (ESI): m/z 629 [M+H]$^+$.

Example 6

N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1-(4-(trifluoromethyl)phenyl)-1H-1,2,3-triazole-4-carboxamide (8n)

To a solution of 1-(4-(trifluoromethyl)phenyl)-1H-1,2,3-triazole-4-carboxylic acid (128.5 mg, 0.5 mmol) in dry dimethylformamide, EDCI (115 mg, 0.6 mmol) and HOBT (81 mg, 0.6 mmol) were added at 0° C. and the reaction mixture was stirred for 20 min. To the reaction mixture 4β-amino phodophyllotoxin (206.5 mg, 0.5 mmol) was added and stirred at room temperature for 12 h. The contents of the reaction mixture were poured into ice-cold water (25 mL), extracted with ethyl acetate (3×15.0) and the combined organic phase was washed with brine, dried over anhydrous sodium sulfate, filtered and concentrated in vacuo. The obtained residue was purified by column chromatography using ethyl acetate-hexane (0-50%) as eluent to give 258 mg (79%) of analytically pure compound (8n). mp: 190-194° C.; $[\alpha]^{25}_D$: −93.6 (c:3.9, CHCl3); MS (ESI): m/z 653 [M+H]$^+$.

Example 7

1-(4-chlorophenyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (8p)

To a solution of 1-(4-chlorophenyl)-1H-1,2,3-triazole-4-carboxylic acid (111.5 mg, 0.5 mmol) in dry dimethylformamide, EDCI (115 mg, 0.6 mmol) and HOBT (81 mg, 0.6 mmol) were added at 0° C. and the reaction mixture was stirred for 20 min. To the reaction mixture 4β-amino phodophyllotoxin (206.5 mg, 0.5 mmol) was added and stirred at room temperature for 12 h. The contents of the reaction mixture were poured into ice-cold water (25 mL), extracted with ethyl acetate (3×15.0) and the combined organic phase was washed with brine, dried over anhydrous sodium sulfate, filtered and concentrated in vacuo. The obtained residue was purified by column chromatography using ethyl acetate-hexane (0-50%) as eluent to give 232 mg (75%) of analytically pure compound (8p). mp: 222-225° C.; $[\alpha]^{25}_D$: −72.5 (c:1.2, CHCl3); $^1$H NMR (CDCl3): δ 8.52 (s, 1H), 7.72 (d, J=8.85 Hz, 2H), 7.57 (d, J=8.85 Hz, 2H), 7.52 (d, J=7.47 Hz, 1H), 6.83 (s, 1H), 6.51 (s, 1H), 6.30 (s, 2H), 6.00 (d, J=7.47 Hz, 2H), 5.45 (dd, J=3.35, 7.47 Hz, 1H), 4.60 (d, J=3.35 Hz, 1H), 4.51-4.47 (m, 1H), 3.96-3.91 (m, 1H), 3.81 (s, 3H), 3.76 (s, 6H), 3.08 (m, 2H); MS (ESI): m/z 619 [M+H]$^+$.

Example 8

1-(4-methoxybenzyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (9c)

To a solution of 1-(4-methoxybenzyl)-1H-1,2,3-triazole-4-carboxylic acid (116.5 mg, 0.5 mmol) in dry dimethylformamide, EDCI (115 mg, 0.6 mmol) and HOBT (81 mg, 0.6 mmol) were added at 0° C. and the reaction mixture was stirred for 20 min. To the reaction mixture 4β-amino phodophyllotoxin (206.5 mg, 0.5 mmol) was added and stirred at room temperature for 12 h. The contents of the reaction mixture were poured into ice-cold water (25 mL), extracted with ethyl acetate (3×15.0) and the combined organic phase was washed with brine, dried over anhydrous sodium sulfate, filtered and concentrated in vacuo. The obtained residue was purified by column chromatography using ethyl acetate-hexane (0-50%) as eluent to give 245 mg (78%) of analytically pure compound (9c). mp: 174-177° C.; $[a]^{25}_D$: −72.5 (c:7.6, CHCl3); $^1$H NMR (CDCl3): δ 7.95 (s, 1H), 7.58 (d, J=7.55 Hz, 1H), 7.28 (s, 1H), 6.93 (d, J=8.68 Hz, 2H), 6.80 (s, 1H), 6.44 (s, 1H), 6.30 (s, 2H), 5.98 (d, J=4.72 Hz, 2H), 5.49 (s, 2H), 5.38 (dd, J=3.77, 7.36 Hz, 1H), 4.5 (d, J=4.15 Hz, 1H), 4.46-4.39 (m, 1H), 3.88 (t, J=9.81 Hz, 2H), 3.81 (s, 6H), 3.75 (s, 6H), 3.06-3.00 (m, 2H); MS (ESI): m/z 629 [M+H]$^+$.

Example 9

N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1-(3,4,5-trimethoxybenzyl)-1H-1,2,3-triazole-4-carboxamide (9g)

To a solution of 1-(3,4,5-trimethoxybenzyl)-1H-1,2,3-triazole-4-carboxylic acid (146.5 mg, 0.5 mmol) in dry dimethylformamide, EDCI (115 mg, 0.6 mmol) and HOBT (81 mg, 0.6 mmol) were added at 0° C. and the reaction mixture was stirred for 20 min. To the reaction mixture 4β-amino phodophyllotoxin (206.5 mg, 0.5 mmol) was added and stirred at room temperature for 12 h. The contents of the reaction mixture were poured into ice-cold water (25 mL), extracted with ethyl acetate (3×15.0) and the combined organic phase was washed with brine, dried over anhydrous sodium sulfate, filtered and concentrated in vacuo. The obtained residue was purified by column chromatography using ethyl acetate-hexane (0-50%) as eluent to give 274 mg (79%) of analytically pure compound (9g).). mp: 189-192° C.; $[a]^{25}_D$: −87.9 (c:6.0, CHCl3); $^1$H NMR (CDCl3): δ 8.02 9s, 1H), 8.37 (d, J=7.47 Hz, 1H), 6.78 (s, 1H), 6.54 (d, J=3.66 Hz, 3H), 6.31 (s, 2H), 5.98 (dd, J=1.22, 10.37 Hz, 2H), 5.47 (s, 2H), 5.40 (dd, J=3.96, 7.47 Hz, 1H), 4.64 (d, J=4.27 Hz, 1H), 4.47-4.43 (m, 1H), 3.90-3.87 (m, 1H), 3.86 (s, 6H), 3.85 (s, 3H), 3.81 (s, 3H), 3.75 (s, 6H), 3.06-3.01 (m, 2H); MS (ESI): m/z 689 [M+H]$^+$.

Example 10

1-(4-chlorobenzyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (9p)

To a solution of 1-(4-chlorobenzyl)-1H-1,2,3-triazole-4-carboxylic acid (119 mg, 0.5 mmol) in dry dimethylformamide, EDCI (115 mg, 0.6 mmol) and HOBT (81 mg, 0.6 mmol) were added at 0° C. and the reaction mixture was stirred for 20 min. To the reaction mixture 4β-amino phodophyllotoxin (206.5 mg, 0.5 mmol) was added and stirred at room temperature for 12 h. The contents of the reaction mixture were poured into ice-cold water (25 mL). extracted with ethyl acetate (3×15.0) and the combined organic phase was washed with brine, dried over anhydrous sodium sulfate, filtered and concentrated in vacuo. The obtained residue was purified by column chromatography using ethyl acetate-hexane (0-50%) as eluent to give 254 mg (80%) of analytically pure compound (9p). mp: 180-184° C.; $[a]^{25}_D$: −87.4 (c:3.7, CHCl3); 1H NMR (CDCl3): δ 8.01 (s, 1H), 7.39 (d, J=8.43 Hz, 2H), 7.39-7.35 (m, 1H), 7.24 (d, J=8.43 Hz, 2H), 6.78 (s, 1H), 6.54 (s, 1H), 6.31 (s, 2H), 5.98 (dd, J=1.2, 8.9 Hz, 2H), 5.54 (s, 2H), 5.40 (dd, J=3.7, 7.5 Hz, 1H), 4.63 (d, J=4.03 Hz, 1H), 4.46-4.42 (m, 1H), 3.92-3.86 (m, 1H), 3.81 (s, 3H), 3.75 (s, 6H), 3.06-3.01 (m, 2H); MS (ESI): m/z 633 [M+H]$^+$.

Biological Activity:

The in vitro cytotoxic activity studies for these 4β-amidotriazole linked podophyllotoxin analogues were carried out at the Chemical Biology, CSIR-Indian Institute of Chemical Technology, Hyderabad, India.

Cytotoxic Activity

4β-Amidotriazole linked podophyllotoxin derivatives of general formulae 8a-z and 9a-z have been evaluated for their in vitro cytotoxicity in selected human cancer cell lines i.e., Cervical (Hela), Breast (MCF-7), Prostate (DU-145), Lung (A549), Liver (HepG2) and Colon (HT-29) using MTT assay and the values obtained were compared to a standard drug like etoposide, with the concentration (treatment done at ranging from $10^{-4}$ to $10^{-8}$ M) of the compound produces to 50% inhibition of cell growth ($IC_{50}$) as shown in Table 1. The screening results suggested that the selected compounds 8a, 8c, 8n, 8p, 9c and 9p exhibits significant cytotoxicity against a different set of human cancer cell lines. The $IC_{50}$ values (in μM) for compounds 8a, 8c, 8n, 8p, 9c and 9p have been illustrated in Table 1.

From the Table. 1 it seen that compounds 8a, 8c, 8n, 8p, 9c and 9p exhibited significant activity against all tested human cancer cell lines, with $IC_{50}$ values ranging from 0.70 to 4.0 μM. Predominantly, the given compounds 8a, 8c, 8n, 8p, 9c and 9p showing superior cytotoxicity than standard drug etoposide in different cancer cell lines. Moreover, compound 8p exhibits remarkable cytotoxicity value i.e. 0.70-4.11 μM than the other compounds revealed in the Table 1. Briefly, the different cancer cell lines i.e. Cervical (Hela), Breast (MCF-7), Prostate (DU-145), Lung (A549), Liver (HepG2) and Colon (HT-29) were affected by 8p with $IC_{50}$ values (in μM) 0.78, 0.97, 0.70, 1.20, 0.78 and 4.11 respectively.

TABLE 1

| | | | | | | |
|---|---|---|---|---|---|---|
| IC$_{50}$ values (in μM) for compounds in selected human cancer cell lines | | | | | | |
| Compound[a] | Hela[b] | MCF-7[c] | DU-145[d] | A549[e] | HepG2[f] | HT-29[g] |
| 8a | 2.47 ± 0.24 | 1.45 ± 0.46 | 1.31 ± 0.11 | 1.82 ± 0.11 | 1.94 ± 0.13 | 5.37 ± 0.74 |
| 8c | 6.49 ± 0.22 | 1.11 ± 0.10 | 0.99 ± 0.07 | 1.61 ± 0.38 | 2.79 ± 0.54 | 11.40 ± 1.66 |
| 8n | 1.21 ± 0.27 | 1.35 ± 0.07 | 0.89 ± 0.02 | 1.96 ± 0.08 | 1.21 ± 0.27 | 4.40 ± 0.05 |
| 8p | 0.78 ± 0.02 | 0.97 ± 0.12 | 0.70 ± 0.01 | 1.20 ± 0.01 | 0.78 ± 0.08 | 4.11 ± 0.71 |
| 9c | 3.46 ± 0.06 | 3.32 ± 0.55 | 1.76 ± 0.27 | 5.82 ± 0.43 | 1.96 ± 0.07 | 17.53 ± 0.34 |
| 9p | 3.57 ± 0.16 | 5.30 ± 0.39 | 2.37 ± 0.08 | 8.06 ± 0.06 | 3.54 ± 0.37 | 23.71 ± 0.38 |
| Etoposide | 2.71 ± 0.52 | 1.62 ± 0.14 | 2.35 ± 0.05 | 1.97 ± 0.17 | 2.84 ± 0.27 | 1.87 ± 0.31 |
| Podophyllotoxin | 3.45 ± 0.29 | 3.06 ± 0.24 | 4.15 ± 0.63 | 4.60 ± 0.42 | 6.63 ± 0.17 | 4.78 ± 0.16 |

[a]50% Inhibitory concentration after 48 h of drug treatment and the values are average of three individual experiments,
[b]Human cervical cancer,
[c]Human breast cancer,
[d]Human prostate cancer,
[e]Human lung cancer,
[f]Liver cancer,
[g]Colon cancer.

Significance of the Work Carried Out

The 4β-amidotriazole linked podophyllotoxin analogues that have been synthesized exhibited potent cytotoxic activity against different human tumor cell lines.

ADVANTAGES OF THE INVENTION

Classic antimitotic agents, such as taxanes and vinca alkaloids are widely used to treat human cancers. However, they have certain limitations in their clinical utility due to toxicity, p-glycoprotein-mediated drug resistance, difficult synthesis and isolation procedure. In this present invention, the synthesized compounds have shown significant anticancer activity with least toxic to normal cells.

The present invention provides a new 4β-amidotriazole linked podophyllotoxin derivatives useful as antitumor agents.

It also provides a process for the preparation of novel 4β-amidotriazole linked podophyllotoxin derivatives.

We claim:

1. A compound of 4β-Amidotriazole linked podophyllotoxin congeners of general formula A:

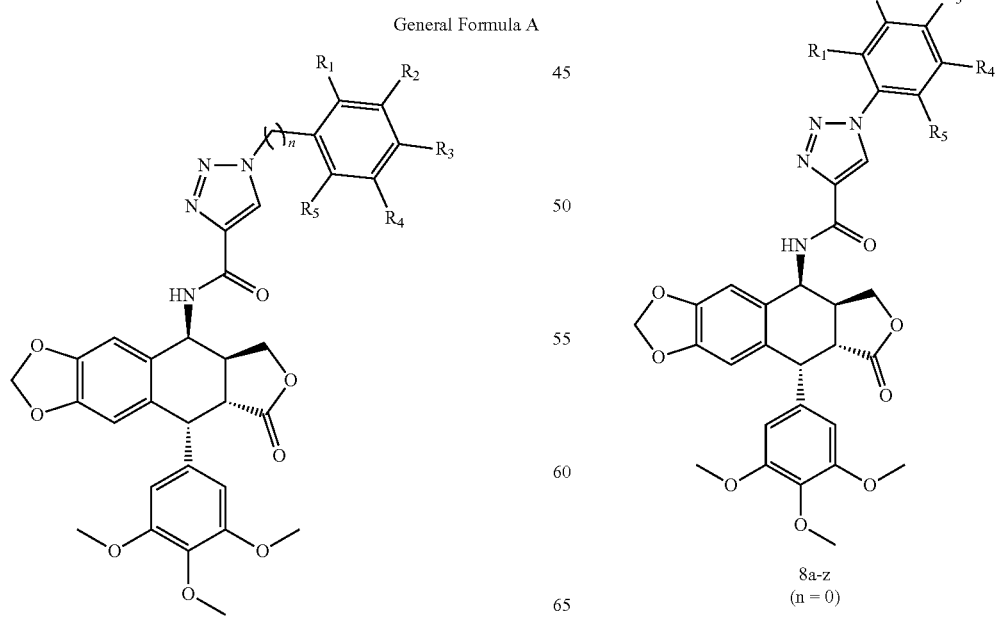

General Formula A wherein n=0,1 and $R_1$-$R_5$=[H, Cl, F, $CH_3$, $OCH_3$, 3,4(-$OCH_2O$—), $CF_3$, $OCF_3$, m-$OC_6H_5$, OH].

2. The compounds as claimed in claim 1, wherein the compounds are represented as:

8a-z (n = 0)

-continued

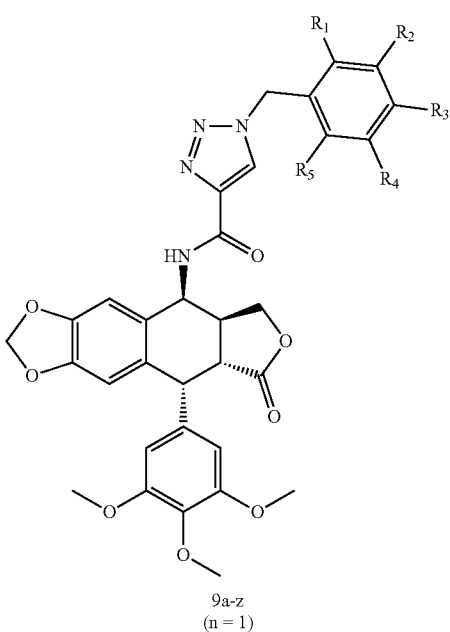

A2

9a-z
(n = 1)

wherein
R$_1$-R$_5$=[H, Cl, F, CH$_3$, OCH$_3$, 3,4(-OCH$_2$O—), CF$_3$, OCF$_3$, m-OC$_6$H$_5$, OH].

3. The compound as claimed in claim 1, wherein the compound is selected from the group consisting of:
N-((5S, 5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1-phenyl-1H-1,2,3-triazole-4-carboxamide (8a)
1-(3-methoxyphenyl)-N-((5S,5aS,8aR,9R)-8-oxo-9-(3,4,5-trimethoxyphenyl) -5,5a,6,8,8a,9-hexahydrofuro[3',4':6,7]naphtho[2,3-d][1,3]dioxol-5-yl)-1H-1,2,3-triazole-4-carboxamide (8b)
1-(4-methoxyphenyl)-N-((5S,5aS,8aR,9R)-8-oxo-9-(3,4,5-trimethoxyphenyl) -5,5a,6,8,8a,9-hexahydrofuro[3',4':6,7]naphtho[2,3-d][1,3]dioxol-5-yl)-1H-1,2,3-triazole-4-carboxamide (8c)
1-(3,4-dimethoxyphenyl)-N-((5S,5aS,8aR,9R)-8-oxo-9-(3,4,5-trimethoxyphenyl) -5,5a,6,8,8a,9-hexahydrofuro[3',4':6,7]naphtho[2,3-d][1,3]dioxol-5-yl)-1H-1,2,3-triazole-4-carboxamide (8d)
1-(3,5-dimethoxyphenyl)-N-((5S,5aS,8aR,9R)-8-oxo-9-(3,4,5-trimethoxyphenyl) -5,5a,6,8,8a,9-hexahydrofuro[3',4':6,7]naphtho[2,3-d][1,3]dioxol-5-yl)-1H-1,2,3-triazole-4-carboxamide (8e)
1-(2,4-dimethoxyphenyl)-N-((5S,5aS,8aR,9R)-8-oxo-9-(3,4,5-trimethoxyphenyl) -5,5a,6,8,8a,9-hexahydrofuro[3',4':6,7]naphtho[2,3-d][1,3]dioxol-5-yl)-1H-1,2,3-triazole-4-carboxamide (8f)
N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3 ]dioxol-5-yl)-1-(3,4,5-trimethoxyphenyl)-1H-1,2,3-triazole-4-carboxamide (8g)
1-(benzo[d][1,3]dioxol-5-yl)-N-((5S,5aS,8aR,9R)-8-oxo-9-(3,4,5-trimethoxyphenyl) -5,5a,6,8,8a,9-hexahydrofuro[3',4':6,7]naphtho[2,3-d][1,3]dioxol-5-yl)-1H-1,2,3-triazole-4-carboxamide (8h)
1-(4-methoxy-3-methylphenyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (8i)
1-(3-fluoro-4-methoxyphenyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (8j)
1-(3-chloro-4-methoxyphenyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (8k)
N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1-(3-phenoxyphenyl)-1H-1,2,3-triazole-4-carboxamide (8l)
N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1-(3-(trifluoromethyl)phenyl)-1H-1,2,3-triazole-4-carboxamide (8m)
N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1-(4-(trifluoromethyl)phenyl)-1H-1,2,3-triazole-4-carboxamide (8n)
1-(3-chlorophenyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (8o)
1-(4-chlorophenyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (8p)
1-(3-fluorophenyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (8q)
1-(4-fluorophenyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (8r)
N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1-(3-(trifluoromethoxy)phenyl)-1H-1,2,3-triazole-4-carboxamide (8s)
N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1-(4-(trifluoromethoxy)phenyl)-1H-1,2,3-triazole-4-carboxamide (8t)
1-(3,4-difluorophenyl)-N-((5S,5aS,8aR,9R)-8-oxo-9-(3,4,5-trimethoxyphenyl) -5,5a,6,8,8a,9-hexahydrofuro[3',4':6,7]naphtho[2,3-d][1,3]dioxol-5-yl)-1H-1,2,3-triazole-4-carboxamide (8u)
1-(3,4-dichlorophenyl)-N-((5S,5aS,8aR,9R)-8-oxo-9-(3,4,5-trimethoxyphenyl) -5,5a,6,8,8a,9-hexahydrofuro[3',4':6,7]naphtho[2,3-d][1,3]dioxol-5-yl)-1H-1,2,3-triazole-4-carboxamide (8v)
1-(4-hydroxyphenyl)-N-((5S,5aS,8aR,9R)-8-oxo-9-(3,4,5-trimethoxyphenyl) -5,5a,6,8,8a,9-hexahydrofuro[3',4':6,7]naphtho[2,3-d][1,3]dioxol-5-yl)-1H-1,2,3-triazole-4-carboxamide (8w)
N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1-(p-tolyl)-1H-1,2,3-triazole-4-carboxamide (8x)
1-(3-hydroxy-4-methoxyphenyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (8y)
1-(4-chloro-3-fluorophenyl)-N-((5S,5aS,8 aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (8z)

1-benzyl-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (9a)

1-(3-methoxybenzyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (9b)

1-(4-methoxybenzyl)-N-((5S,5aS,8aR,9R)-8-oxo-9-(3,4,5-trimethoxyphenyl) -5,5a,6,8,8a,9-hexahydrofuro[3',4':6,7]naphtho[2,3-d][1,3]dioxol-5-yl)-1H-1,2,3-triazole-4-carboxamide (9c)

1-(3,4-dimethoxybenzyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (9d)

1-(3,5-dimethoxybenzyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (9e)

1-(2,4-dimethoxybenzyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (9f)

N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1-(3,4,5-trimethoxybenzyl)-1H-1,2,3-triazole-4-carboxamide (9g)

1-(benzo[d][1,3]dioxol-5-ylmethyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (9h)

1-(3-methoxy-4-methylbenzyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (9i)

1-(3-fluoro-4-methoxybenzyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (9j)

1-(3-chloro-4-methoxybenzyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (9k)

N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1-(3-phenoxybenzyl) -1H-1,2,3-triazole-4-carboxamide (9l)

N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1-(3-(trifluoromethyl)benzyl)-1H-1,2,3-triazole-4-carboxamide (9m)

N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1-(4-(trifluoromethyl)benzyl)-1H-1,2,3-triazole-4-carboxamide (9n)

1-(3-chlorobenzyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (9o)

1-(4-chlorobenzyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (9p)

1-(3-fluorobenzyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (9q)

1-(4-fluorobenzyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (9r)

N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1-(3-(trifluoromethoxy)benzyl)-1H-1,2,3-triazole-4-carboxamide (9s)

N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1-(4-(trifluoromethoxy)benzyl)-1H-1,2,3-triazole-4-carboxamide (9t)

1-(3,4-difluorobenzyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (9u)

1-(3,4-dichlorobenzyl)-N-((5S,5aS,8aR,9R)-8-oxo-9-(3,4,5-trimethoxyphenyl) -5,5a,6,8,8a,9-hexahydrofuro[3',4':6,7]naphtho[2,3-d][1,3]dioxol-5-yl)-1H-1,2,3-triazole-4-carboxamide (9v)

1-(4-hydroxybenzyl)-N-((5S,5aS,8aR,9R)-8-oxo-9-(3,4,5-trimethoxyphenyl) -5,5a,6,8,8a,9-hexahydrofuro[3',4':6,7]naphtho[2,3-d][1,3]dioxol-5-yl)-1H-1,2,3-triazole-4-carboxamide (9w)

1-(4-methylbenzyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (9x)

1-(3-hydroxy-4-methoxybenzyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (9y)

1-(4-chloro-3-fluorobenzyl)-N-((5S,5aS,8aR,9R)-8-oxo-9-(3,4,5-trimethoxyphenyl)-5,5a,6,8,8a,9-hexahydrofuro[3',4':6,7]naphtho[2,3-d][1,3]dioxol-5-yl)-1H-1,2,3-triazole-4-carboxamide (9z).

4. The compound as claimed in claim 1, wherein the structural formulae of the compounds are:

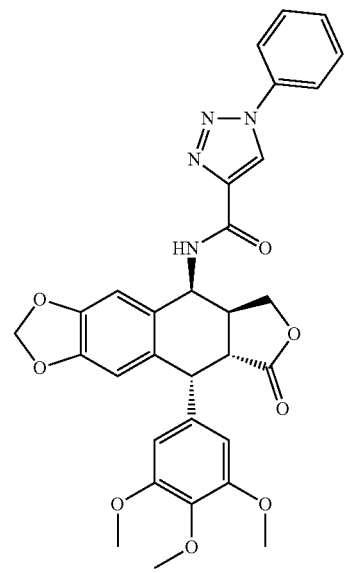

8a

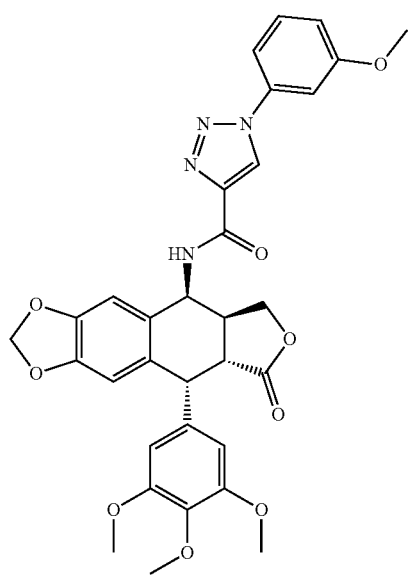
8b
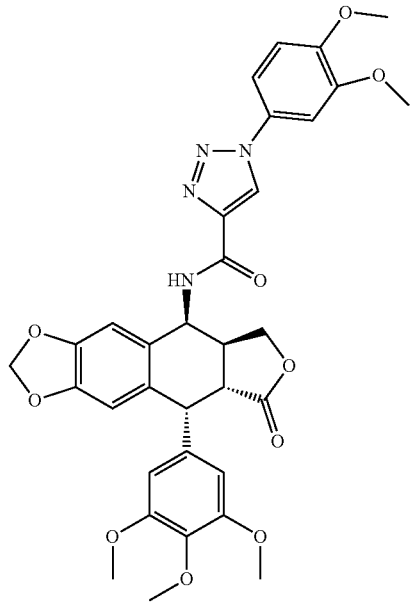
8d
8c
8e

8f
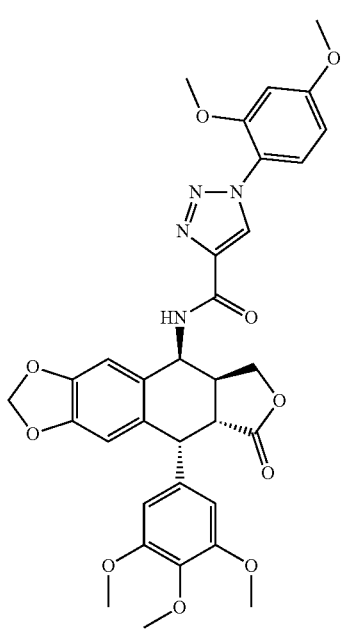
8h
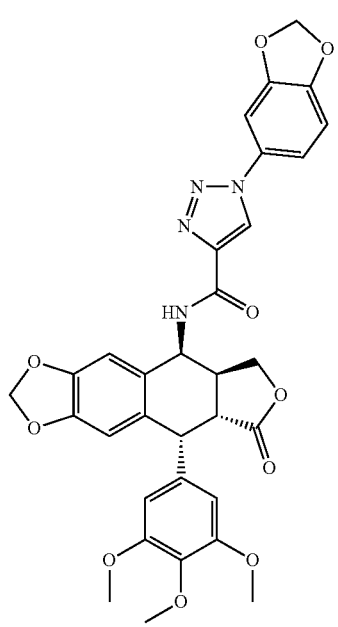
8g
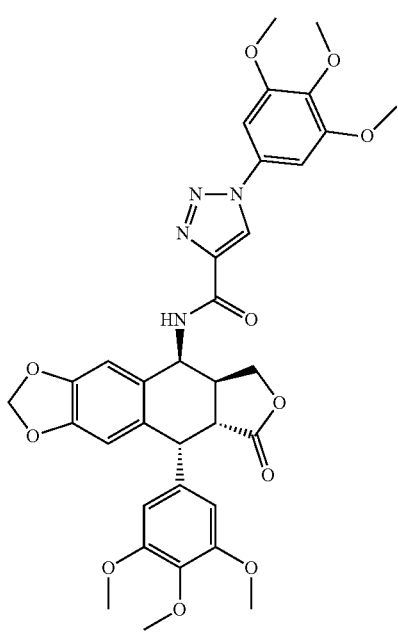
8i
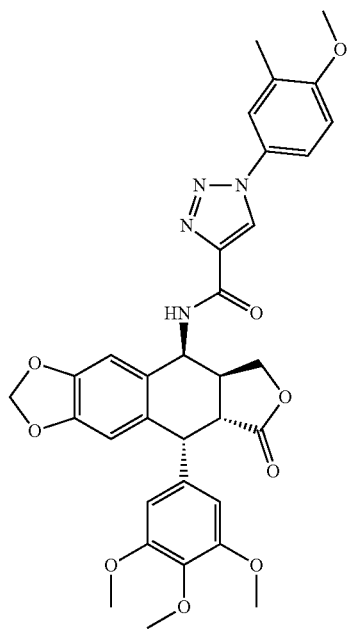

8j
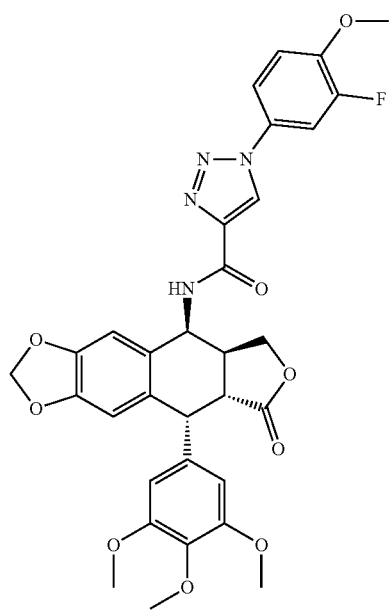
8k
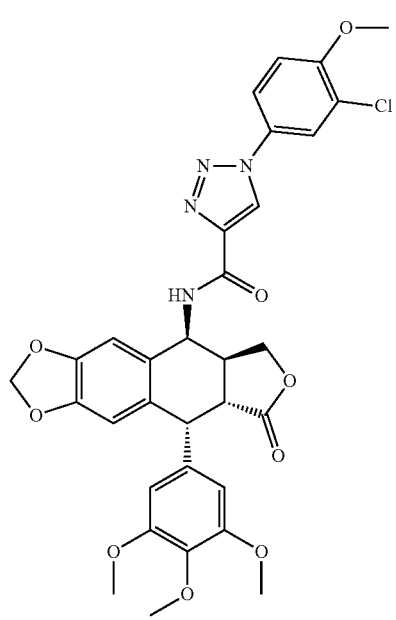
8l
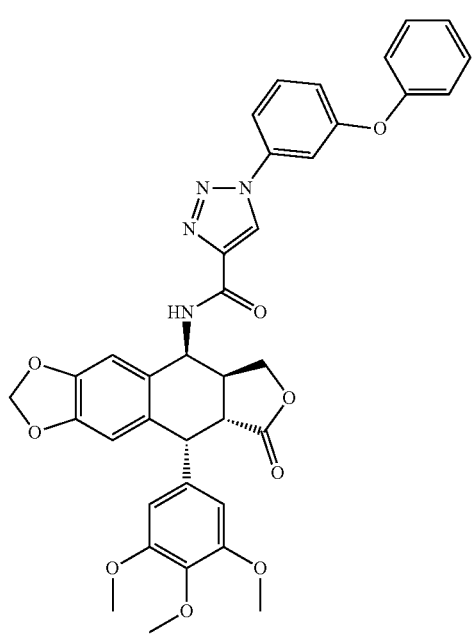
8m
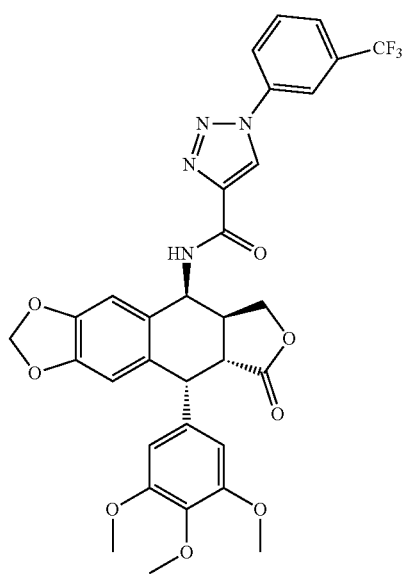

27
-continued
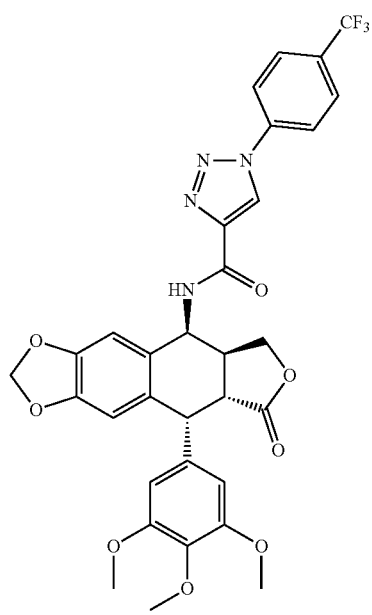
8n
28
-continued
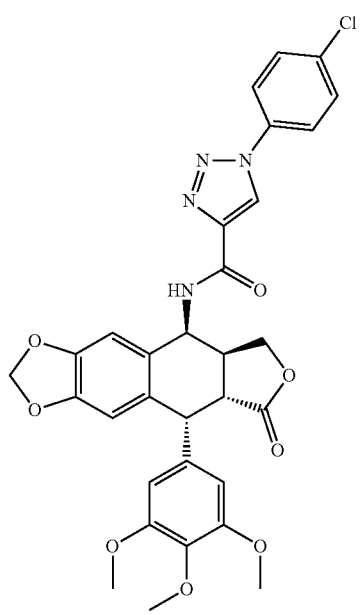
8p
8o
8q

-continued
8r
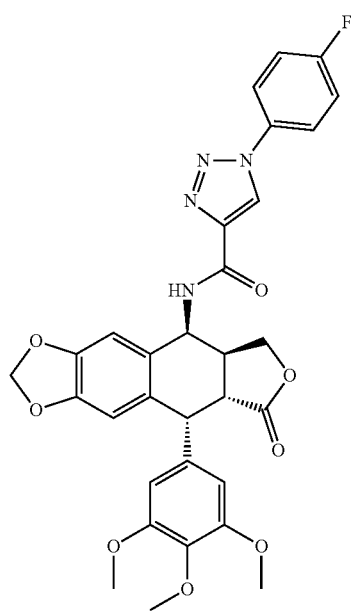
8t
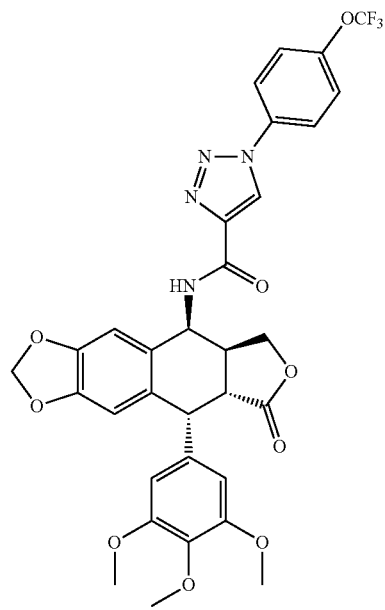
8s
8u

31
-continued
8v
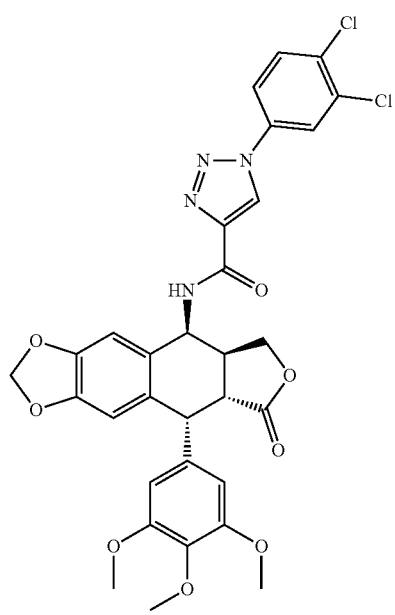
32
-continued
8x
8w
8y
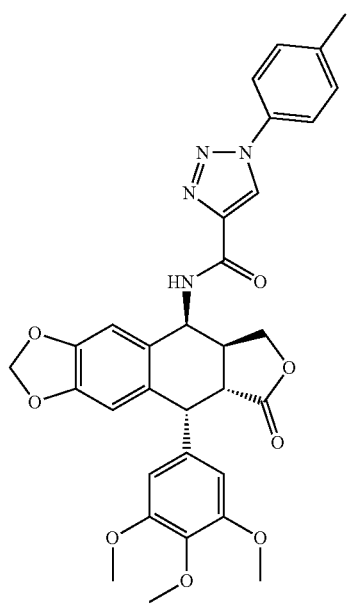

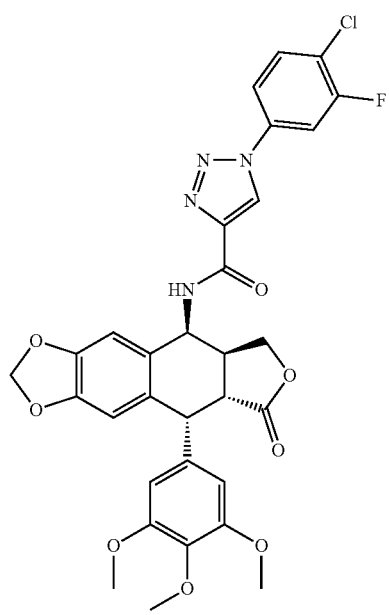
8z
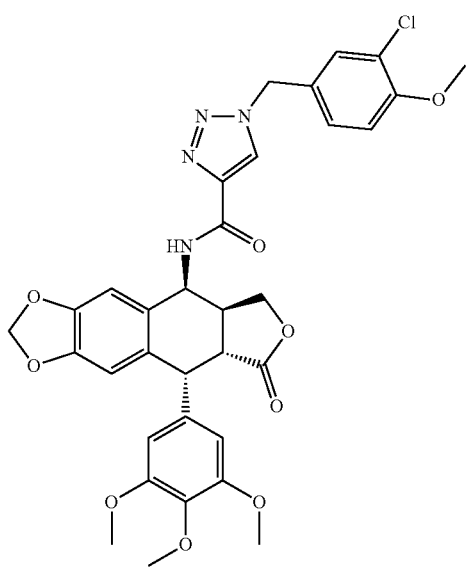
9k
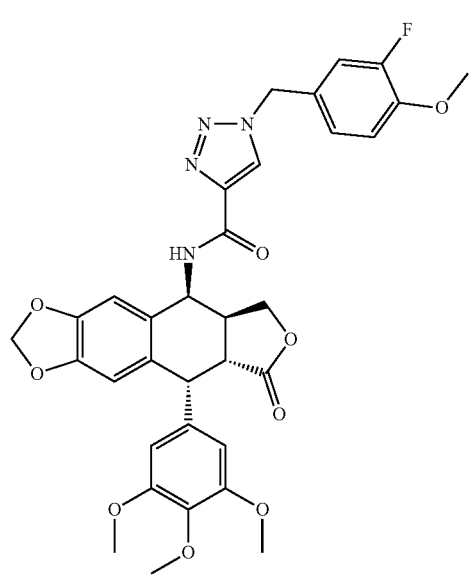
9j
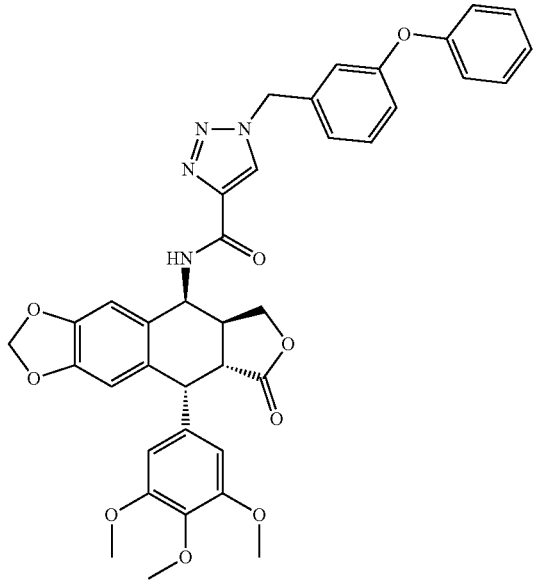
9l

35
-continued
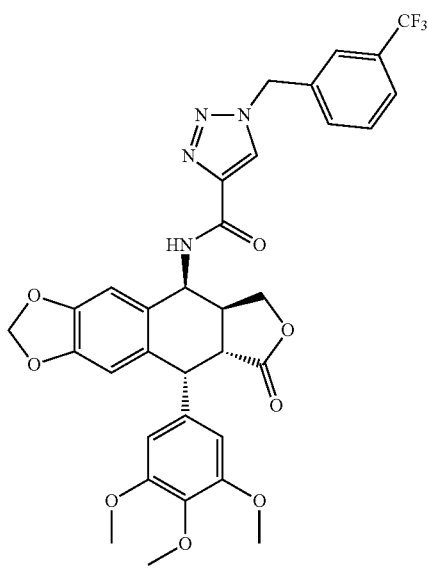
9m
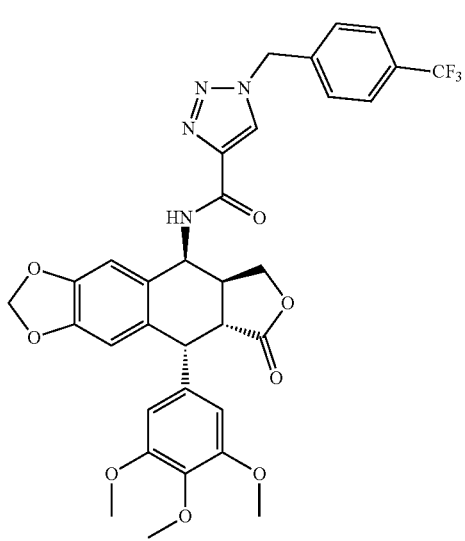
9n
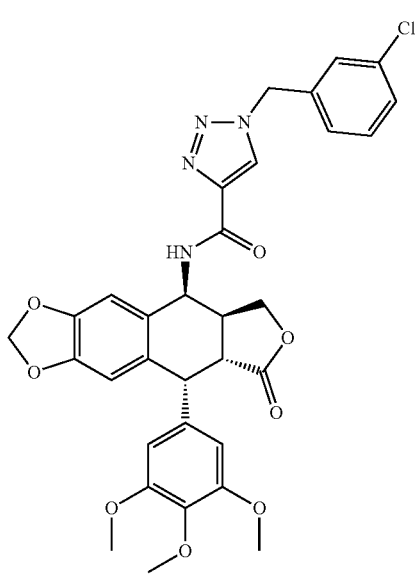
9o
36
-continued
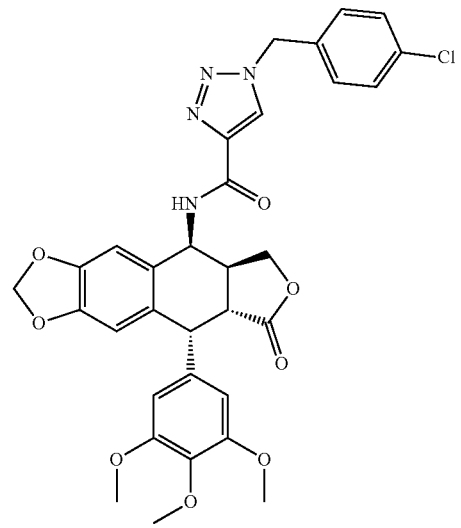
9p
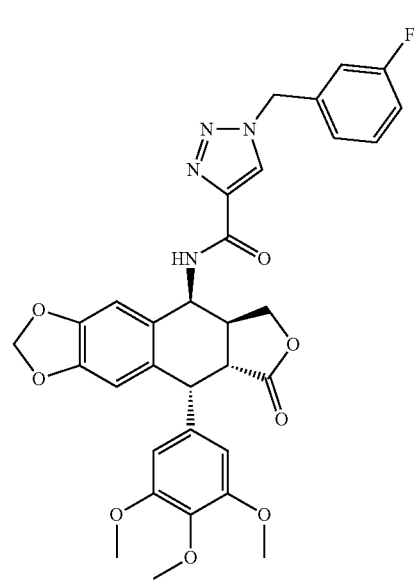
9q
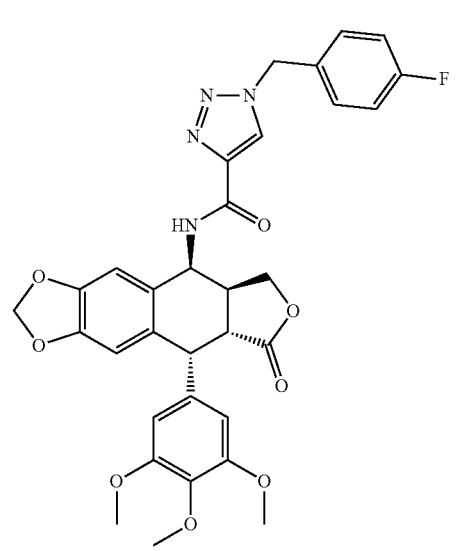
9r 37
-continued
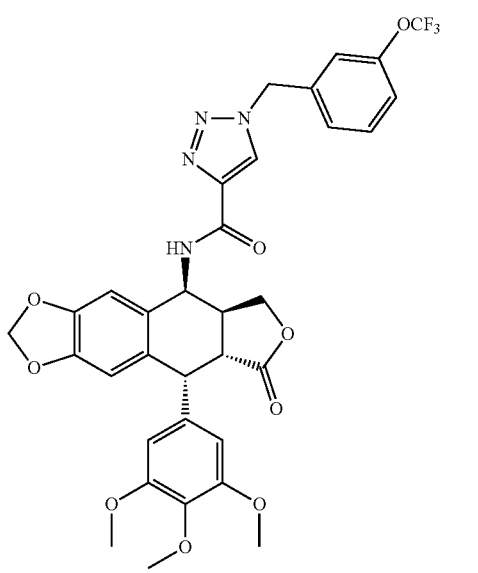
9s
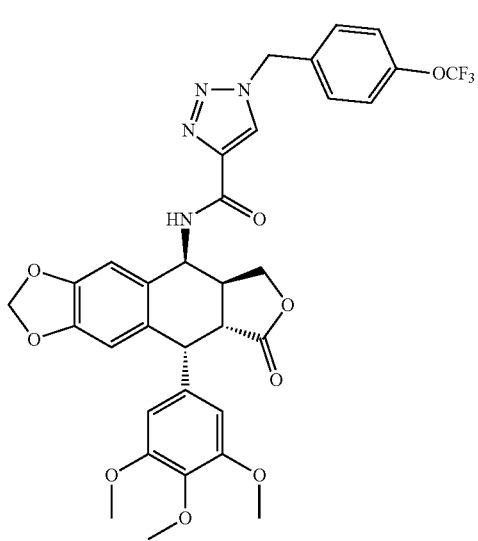
9t
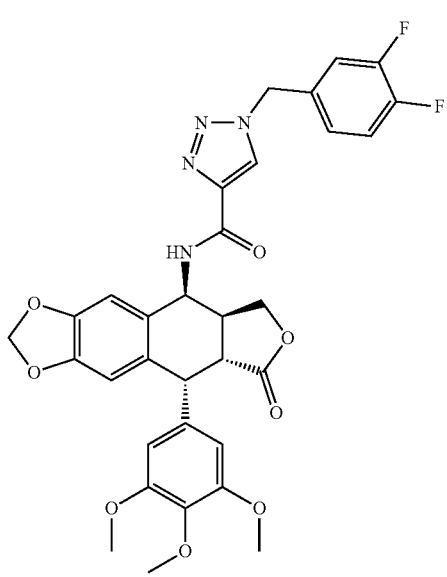
9u
38
-continued
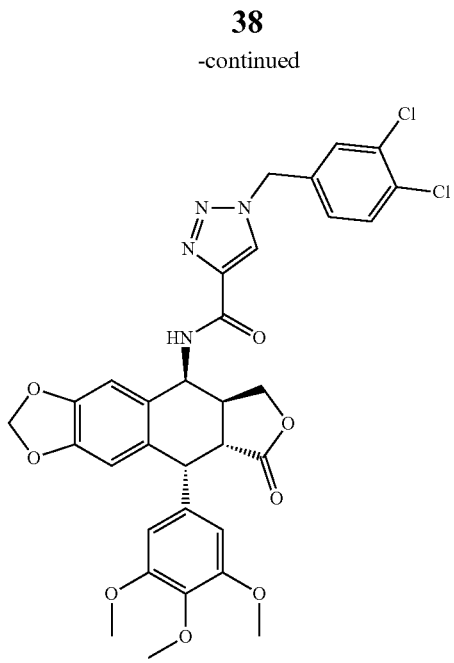
9v
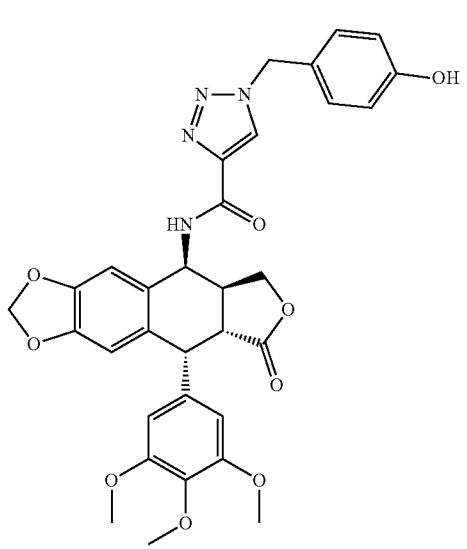
9w
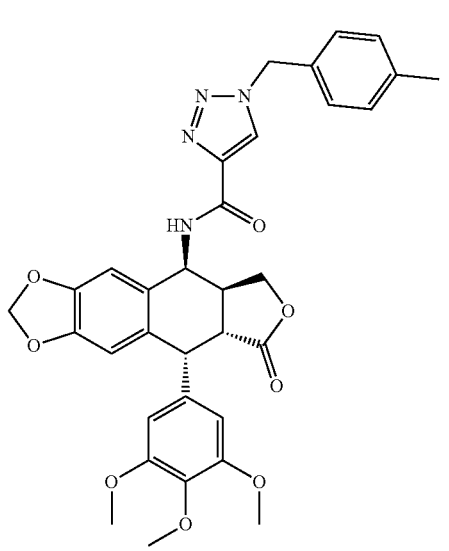
9x 9y
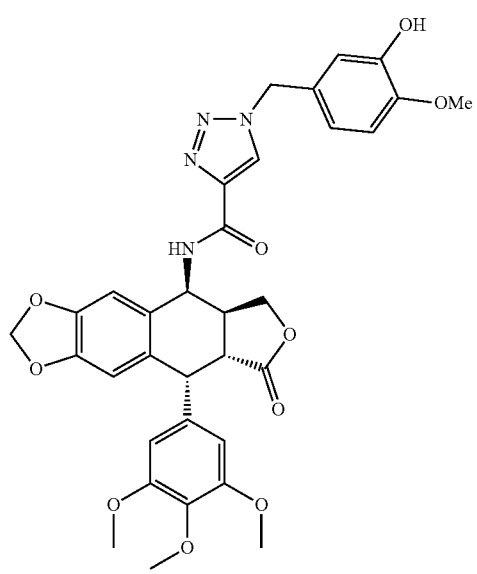
9z
5c or 6c
5d or 6d
5e or 6e
5f or 6f
5g or 6g
5h or 6h
5i or 6i
5j or 6j
5k or 6k
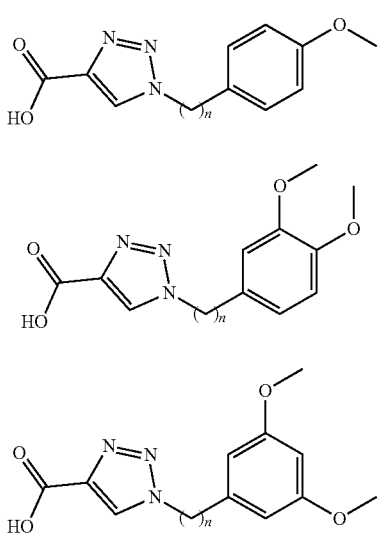
5. A process for the preparation of the compounds as claimed in claim 1, wherein the process comprises the steps of:
   i. reacting the compound of formula 5a-z and 6a-z
5a or 6a
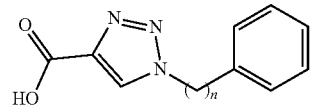
5b or 6b
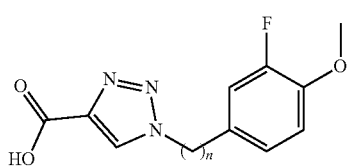
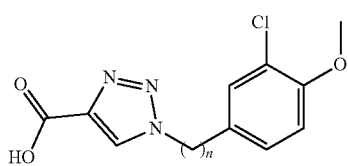

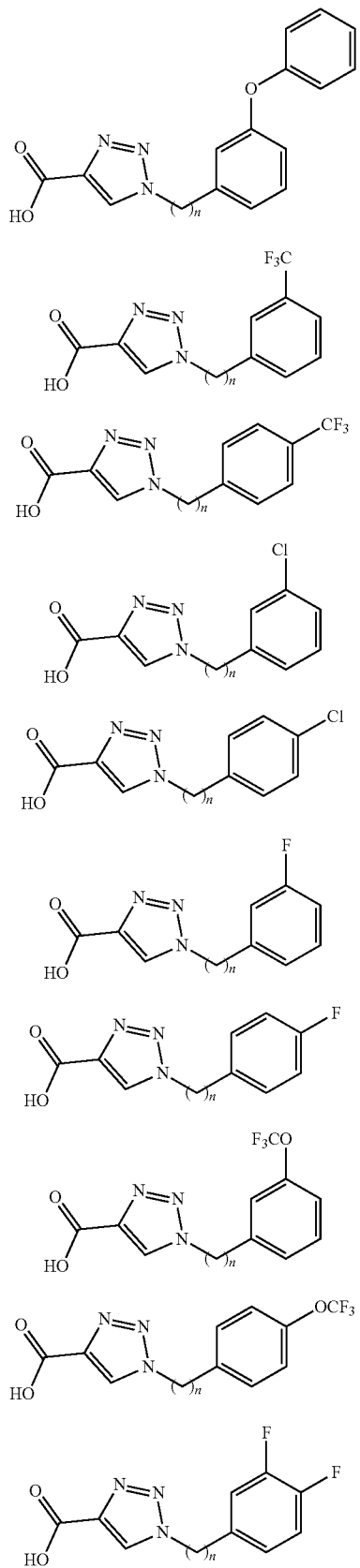

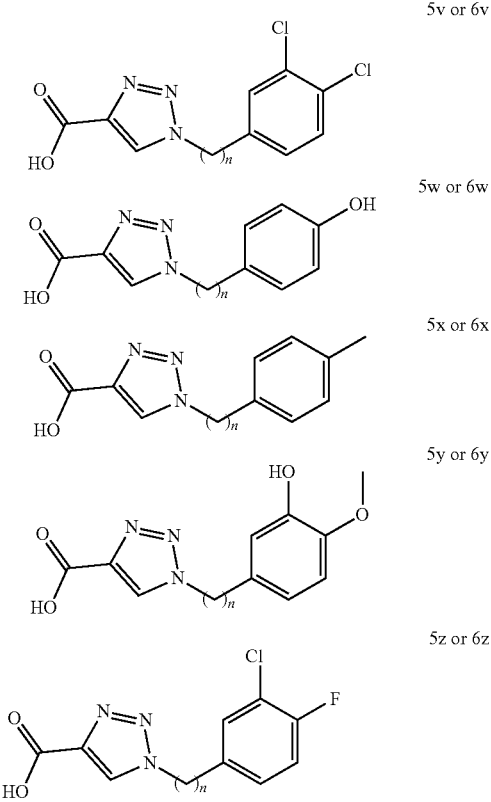

wherein, n is 0 in the 5a-5z;

n is 1 in the 6a-6z, with EDC, HOBT in dry DMF under nitrogen atmosphere to obtain reaction mixture;

ii. stirring the reaction mixture as obtained in step (i) at a temperature 0° C. for a time period of 20 min to obtain mixture;

iii. stirring the mixture at room temperature for 12 hours as obtained in step (ii) with compound of formula 7

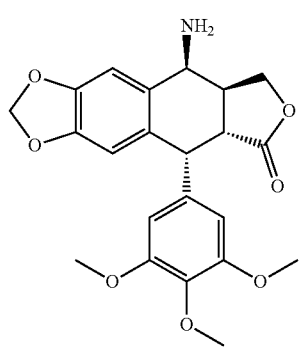

followed by extraction and purification to obtain the compound of General Formula A as claimed in claim 1.

* * * * *